United States Patent [19]

Sagen et al.

[11] Patent Number: 4,980,174

[45] Date of Patent: Dec. 25, 1990

[54] METHOD FOR ALLEVIATING DEPRESSION

[76] Inventors: Jacqueline Sagen, 2509 W. Farwell, Chicago, Ill. 60645; Caryl E. Sortwell, 4548 N. Sheridan, Chicago, Ill. 60640; George D. Pappas, 506 W. Roscoe St., Chicago, Ill. 60657

[21] Appl. No.: 289,609

[22] Filed: Dec. 23, 1988

[51] Int. Cl.⁵ .................. A61K 35/30; A61K 35/55; A61B 17/00
[52] U.S. Cl. ..................................... 424/563; 424/520; 424/570; 604/49; 128/897; 128/898
[58] Field of Search ................ 424/95, 113, 520, 563, 424/570; 604/49; 128/897, 898

[56] References Cited

U.S. PATENT DOCUMENTS 4,753,635  6/1988  Sagen et al. ..................... 514/818

OTHER PUBLICATIONS

Goodman & Gilman's, *The Pharmacological Basis of Therapeutics,* 7th ed., MacMillan Publ. Co., New York, 1985, pp. 412–413 & 423–426.
Madrazo et al., "Open Microsurgical Autograft . . . Parkinson's Disease", New Eng. J. Med., 316(14):831–834, (1987).
Telner et al., 1984, J. Psychiat. Res., 18:207–215.
Wilner, 1985, Depression, A Psychobiol. Synthesis, John Wiley & Sons, p. 137.
Wilner, 1986, Prog. Neuropsychopharmacol. Biol. Psychiat., 10:677–690.
Nair et al., 1989, Psychiatr. J., 14:328–341.
Jesberger et al., 1985, Inter. J. Neurosci., 27:19–47.
Paykel, 1989, British J. Psychiat., 155:754–763.
Fitten et al., 1989, JAGS, 37:459–472.
Goodman & Gilman's Pharmacological Basis of Therapeutics, 7th Edition, p. 423.

*Primary Examiner*—Jacqueline Stone
*Assistant Examiner*—Jean Witz
*Attorney, Agent, or Firm*—Mishrilal L. Jain

[57] ABSTRACT

A novel method for alleviating depression comprises implanting monoamine producing living cells in the CNS of depressive subjects.

9 Claims, 2 Drawing Sheets

METHOD FOR ALLEVIATING DEPRESSION

Depression is the most common of the major mental illnesses. It is characterized by feelings of prolonged intense sadness and despair without an apparent cause, and is often accompanied by mental and physical disruption, including loss of concentration, pessimism, insomnia, weight loss, and decreased energy. A significant percentage of patients with this disorder display suicidal behavior during their lifetime. Many of these patients respond well to tricyclic antidepressants, the treatment of choice for this condition. Although quite effective in many patients, the efficacy is dependent on continued long-term drug usage. This condition cannot always be guaranteed due to patient non-compliance and numerous unpleasant side effects.

It has been reported that behavior can be altered by transplanting pharmacologically relevant tissues into the central nervous system (for review, see Azmitia and Bjorklund, 1987 Ann. N.Y. Acad. Sci. 495: 813). For example, it has been shown that sensitivity to pain can be reduced by transplanting opioid peptide-containing cells into pain modulatory regions of the CNS (Sagen et al. 1987 Exp. Brain Res. 67: 373–379). Other laboratories have shown that it is possible to alleviate cognitive or motor deficits in lesioned animals following neural transplantation. The latter studies have led to clinical trials for the alleviation of Parkinson's disease symptoms using neutral transplantation (Backlund et al. 1987 Ann. N.Y. Acad. Sci. 495: 658–670). However, there is no prior report that depression can be alleviated by CNS transplantation.

SUMMARY OF THE INVENTION

It is, therefore, an object of the present invention to provide a method for alleviating depression by transplanting live monoamine-containing cells into the central nervous system (CNS) where a source of monoamines is needed.

Other objects and advantages will become evident from the following detailed description of the invention.

BRIEF DESCRIPTION OF DRAWINGS

These and other objects, features and many of the attendant advantages of the invention will be better understood upon a reading of the following detailed description when considered in connection with the accompanying drawings wherein.

DETAILED DESCRIPTION OF THE INVENTION

Figure 1:
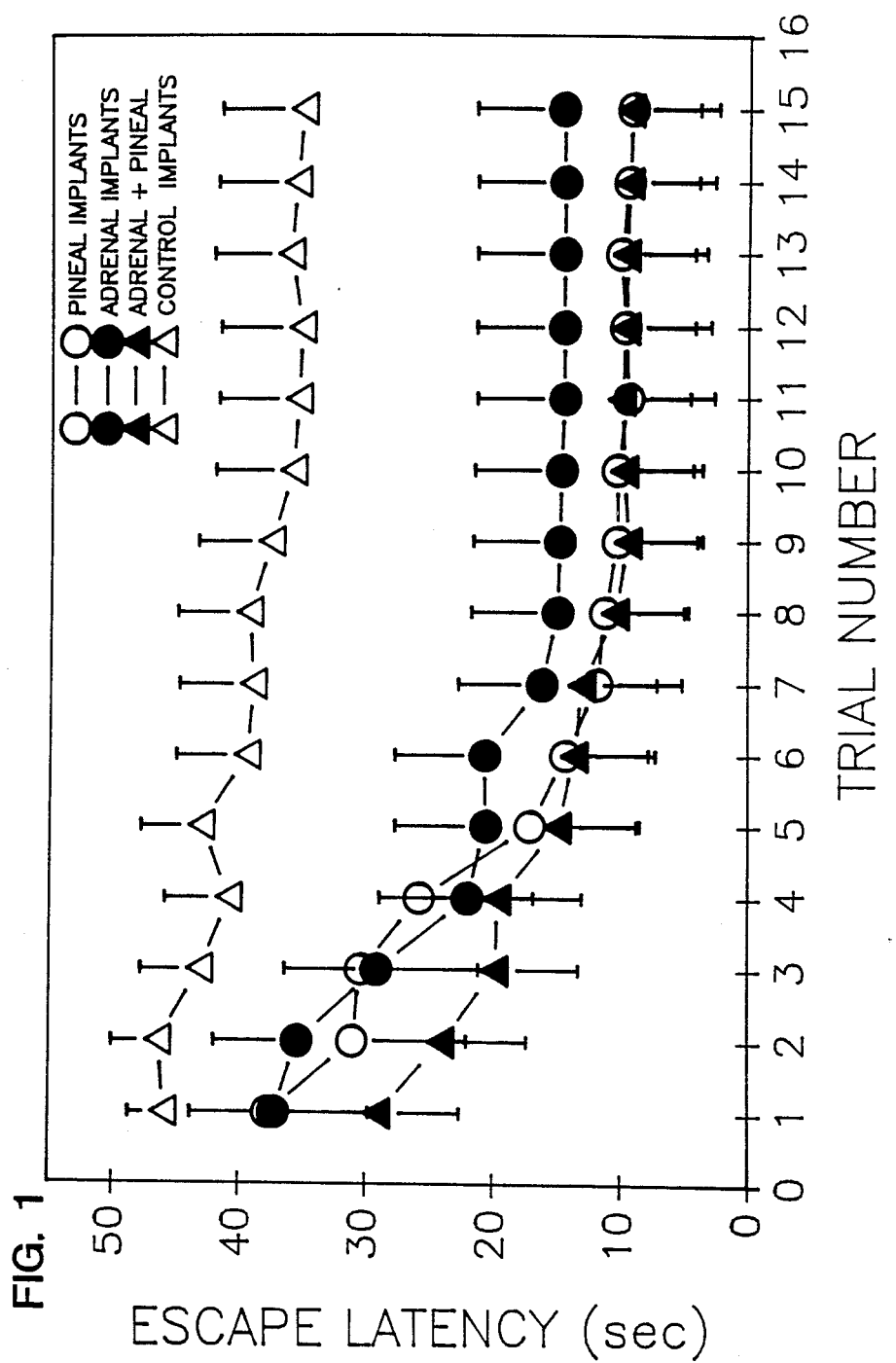
FIG. 1 shows the effect of frontal cortex transplants in rats on escape latencies in a shuttle box following learned helplessness training. The ordinate is the trial number in the shuttle box 24 hours after training with inescapable shock. Rats received 15 consecutive escape trials in the shuttle box. Latency to escape to the non-shock side of the shuttle box (abscissa) was measured following the onset of shock for each trial. Animals which failed to escape were assigned a maximum escape latency of 50 sec. Groups of animals included pineal transplants (open circles; n=7), adrenal medullary transplants (filled circles; n=11), adrenal medulla+pineal transplants (filled triangles; n=12), and control transplants (open triangles; n=13) in the rat frontal cortex. Values represent the means +/−S.E.M. for each group.

The above and various other objects and advantages of the present invention are achieved by implanting live monoamine-producing cells in one or more regions of the central nervous system of a subject showing symptoms of depression.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed herein are standard methodologies well known to one of ordinary skill in the art.

The theory for the cause of major depression states that there is a deficit in brain biogenic amine systems, serotonin and norepinephrine postulated to be particularly involved. The CNS levels of these transmitters are increased by tricyclic antidepressant treatment, as well as other therapies for major depression, including monoamine oxidase inhibitors and electroconvulsive shock treatment. The present invention takes a different approach. The invention employs transplanting of monoamine-producing cells into the brain to provide a local source of monoamines for the permanent alleviation of depression. The invention is based on the finding that such transplants are able to prevent the development of learned helplessness, a well-established animal model for depression.

Learned helplessness (originally described by Seligman and co-workers in dogs, and subsequently extended to a large number of other species including rats) is the condition that results from exposure to inescapable and uncontrollable stress which produces deficits in subsequent performance when the stress is escapable and controllable (Seligman and Maier, 1967, J. Exp. Psychol. 74: 1–9; Seligman and Beagley, 1975, J. Comp. Physiol. Psychol. 88: 534–541). In contrast, if the original stress is controllable, these deficits do not develop. The theory of learned helplessness is predicated on a number of parallels between clinical depression and laboratory observations, including weight loss, lethargy, and decreased motivation, as well as similarities in treatment and biochemistry (Willner, 1986, Prog. Neuro-Psychopharm. and Biol. Psychiat. 10: 677–690). This model has been shown to have good predictive validity for treatment of human depression, as it is reversed by administration of tricyclic antidepressants and electroconvulsive shock treatment, and monamine oxidase inhibitors, but not by psychoactive drugs which are ineffective in treating depression in humans, including anxiolytics, neuroleptics, stimulants, or depressants. The direct injection of tricyclics into several brain regions revealed that either prevention or reversal (Sherman and Petty, 1980, Behav. Neural Biol. 30: 119-134; Sherman et al, 1982, Pharmacol. Biochem. Behav. 16: 449-454) of learned helplessness is site-specific, and that the frontal neocortex is one of the critical sites of action for antidepressant activity. Based on these findings, the present invention utilized implantation of monoamine-containing cells into the brain to alleviate or reverse depressive condition.

MATERIALS AND METHODS

Male Sprague-Dawley derived rats weighing about 250 g served as hosts for these studies. Sources of monoamine-containing cells included rat pineal gland tissue, rat adrenal medullary tissue, or a combination of these. Cells in the pineal gland are rich in serotonin. In addition, these cells produce high levels of melatonin, an agent that has been associated with certain types of depression known as "seasonal affective disorder". Donor pineal tissue was obtained from adult rat pineal glands, cut into small pieces (less than 0.5 cu. mm.) in Hank's buffer, and transplanted stereotaxically to the rat frontal cortex (coordinates: 3.0 mm, L 2.0 mm, H −1.0 mm, incisor bar −2.5 mm from Bregma). Catecholamine-containing adrenal medullary tissue was dissected from adult rat adrenal glands, cut into pieces and transplanted to the same brain region. In addition, a group of animals were implanted with a combination of tissues from both sources. Although these studies utilized adrenal and pineal tissue as convenient sources of catecholamines and serotonin, respectively, it should be noted that any source of these agents that survive neural transplantation could be used. For example, studies in our laboratory indicate that cell lines producing either serotonin (human colon carcinoma cells, CCL 220) or catecholamines (pheochromocytoma, PC12) are also effective. As a control for these studies, equal volumes of non-catecholamine containing tissues such as striated muscle, sciatic nerve and glioma cells were used.

At 4-6 weeks following tissue implantation, learned helplessness training and testing began. For training, rats were placed on the grid floor of a shock-escape chamber with an inoperative bar press. Preliminary screening in our laboratory showed that animals allowed to terminate shock using the bar press did not become helpless, in contrast to those with an inoperative bar press receiving inescapable shock. Animals received a 2.0 mA shock (via floor grid). Shock is terminated after 50 seconds have elapsed. Following a 50 second interval, inescapable shock was again administered. This training continued for 1 hour, and the animal was returned to its cage. Twenty-four hours after training in the shock chamber, each rat was placed on the active side of a one-way avoidance shuttle box. At the start of each trial, the 2.0 mA shock initiated simultaneously with the opening of the escape panel. The shock was terminated as soon as the rat escaped through the panel to the inactive side of the shuttle box or after 50 seconds had elapsed, whichever occurred sooner. Each rat received fifteen escape trials.

As mentioned before, learned helplessness means the condition that occurs when an animal, after receiving inescapable shock, fails to escape when tested for escape avoidance in a shuttle box. A reversal of the learned helplessness is the test demonstrating the effectiveness of the treatment.

FIG. 1 and Table 1 show the results of the tests conducted. It was found that in animals with control implants in the frontal cortex, only 3 out of 13 escaped in the shuttle box, with an average first escape trial number being 11.5. The other 10 control implanted animals failed to escape at all by trial 15, and remained immobilized in the shock side of the shuttle box for the 50 second shock durations. In contrast, 6 of 7 animals with pineal implants in the frontal cortex escaped, with an average first escape at trial 2.7. Eight of 11 adrenal medulla implanted animals escaped with the average first escape at trial 6.1; and 10 of 12 animals with a combination of pineal and adrenal tissue implanted into the frontal cortex escaped at an average first escape at trial 4.4. The average escape latencies (maximum=50) for all three implant groups over the 15 trials were significantly different ($P<0.01$) than the escape latencies for control implanted animals using 2-way analysis of variance (FIG. 1).

Figure 2B:
FIG. 2B shows adrenal medullary implant in the frontal cortex of a rat which did not become helpless following learned helplessness training. The cells in the adrenal implant are stained with a dopamine-B-hydroxylase antibody and a fluorescein-linked secondary antibody. Magnification=740×.
Figure 2A:
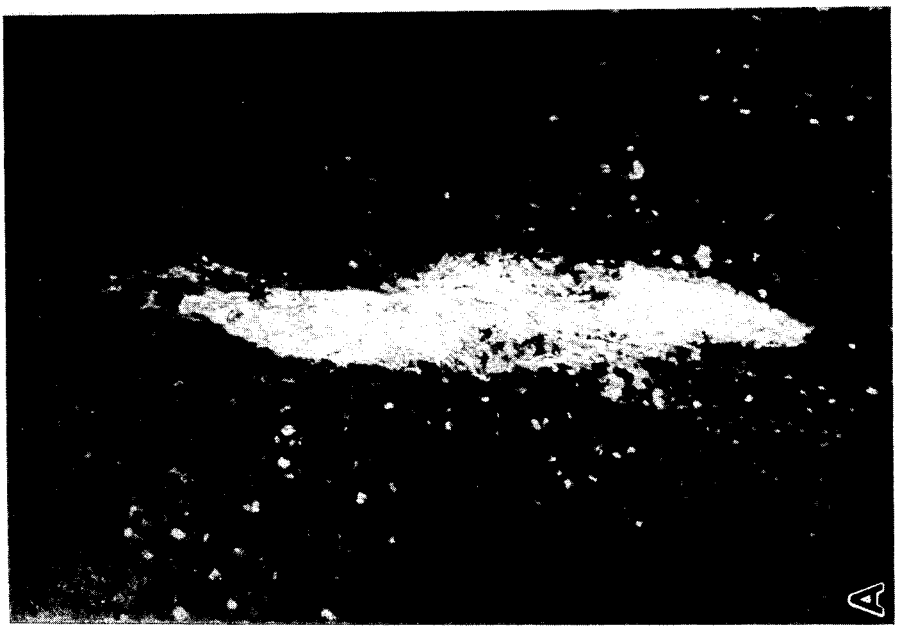
FIG. 2A shows pineal implant in the frontal cortex of a rat which did not become helpless following learned helplessness training. The cells in the pineal implant are stained with a serotonin antibody and a fluorescein-linked secondary antibody. Magnification=740×.

FIG. 2a and b show a pineal (2a) and adrenal medullary (2b) implant in the frontal cortex 8 weeks after surgery and testing. The pineal implant was immunocytochemically stained with a serotonin antibody and fluorescein-linked secondary antibody. The adrenal medullary implant was similarly stained with a dopamine-B-hydroxylase antibody. Control implants did not stain with either antibody. Both the pineal and adrenal implants survived well and retained the ability to produce high levels of their respective monoamines as evidenced by the reversal of the learned helplessness in the implanted animals.

Since learned helplessness is a widely used model for human clinical depression and for screening antidepressant therapies, the results obtained by the methodology of the present invention clearly indicate treating clinical depression using monoamine neural transplants. The advantages of such an approach are the ability to provide a permanent source of monoamines in local brain regions such as the frontal cortex, limbic regions, ventricular spaces and the like, and a commensurate reduced need for repeated administration of pharmacological agents which often have undesirable side effects.

It is understood that the examples and embodiments described herein are for illustrative purposes only and that various modifications or changes in light thereof will be suggested to persons skilled in the art and are to be included within the spirit and purview of this application and scope of the appended claims.

TABLE 1

| GROUP | N | NUMBER OF ESCAPING ANIMALS | PERCENT OF ANIMALS ESCAPING | AVERAGE TRIAL TO ESCAPE (cutoff = 15) |
|---|---|---|---|---|
| Pineal Implants | 7 | 6 | 86% | 2.7 |
| Adrenal Medullary Implants | 11 | 8 | 73% | 6.1 |
| Adrenal + Pineal Implants | 12 | 10 | 83% | 4.4 |
| Control Implants | 13 | 3 | 23% | 11.5 |

What is claimed is:

1. A method for alleviating depressive symptoms, comprising implanting monoamine producing living cells in the central nervous system of a subject exhibiting clinical depression whereby said depressive symptoms are alleviated.

2. The method of claim 1 wherein said cells are selected from the group consisting of pineal gland, adrenal medulla and a combination thereof.

3. The method of claim 1 wherein said central nervous system is the frontal cortex, limbic region or ventricular spaces.

4. The method of claim 2 employing pineal gland cells.

5. The method of claim 2 employing adrenal medullary cells.

6. The method of claim 2 employing a combination of pineal and adrenal medullary cells.

7. The method of claim 3 wherein said central nervous system is the frontal cortex.

8. The method of claim 3 wherein said central nervous system is the limbic region.

9. The method of claim 3 wherein said central nervous system is the ventricular spaces.

* * * * *